United States Patent
Stamminger et al.

(10) Patent No.: US 9,901,653 B2
(45) Date of Patent: Feb. 27, 2018

(54) UV LAMP AND METHOD FOR IRRADIATING A SURFACE, A LIQUID OR A GAS WITH UV RADIATION

(71) Applicants: Heraeus Quarzglas GmbH & Co. KG, Hanau (DE); Heraeus Noblelight GmbH, Hanau (DE)

(72) Inventors: Mark Stamminger, Büdingen (DE); Christoph Söller, Hanau (DE); Franz-Josef Schilling, Freigericht (DE); Erich Arnold, Mainz (DE); Gerhard Schötz, Aschaffenburg (DE); Mario Such, Gräfenhainichen (DE); Andreas Langner, Freigericht (DE); Björn Roos, Freigericht (DE); Klaus Zoltner, Kleinostheim (DE)

(73) Assignees: Heraeus Quarzglas GmbH & Co. KG, Hanau (DE); Heraeus Noblelight GmbH, Hanau (DE)

( * ) Notice: Subject to any disclaimer, the term of this patent is extended or adjusted under 35 U.S.C. 154(b) by 0 days.

(21) Appl. No.: 15/279,641

(22) Filed: Sep. 29, 2016

(65) Prior Publication Data

US 2017/0095583 A1    Apr. 6, 2017

(30) Foreign Application Priority Data

Oct. 1, 2015  (EP) .................................... 15187898

(51) Int. Cl.
*A61N 5/00* (2006.01)
*A61L 2/10* (2006.01)
(Continued)

(52) U.S. Cl.
CPC  *A61L 2/10* (2013.01); *A61L 9/20* (2013.01); *A61N 5/06* (2013.01);
(Continued)

(58) Field of Classification Search
CPC ................................. A61L 2/10; G02B 5/283
(Continued)

(56) References Cited

U.S. PATENT DOCUMENTS

| 5,117,150 A * | 5/1992 | Schwarz | H01J 61/40 313/112 |
| 2010/0277056 A1* | 11/2010 | Kostka | H01J 61/34 313/489 |

(Continued)

FOREIGN PATENT DOCUMENTS

| DE | 647537 C | 7/1937 |
| DE | 3902144 A1 | 8/1990 |

(Continued)

OTHER PUBLICATIONS

Office Action dated Mar. 31, 2016 in EP Application No. 15187898.0.

(Continued)

*Primary Examiner* — Jason McCormack
(74) *Attorney, Agent, or Firm* — Panitch Schwarze Belisario & Nadel LLP

(57) ABSTRACT

A UV lamp including a filter material of doped quartz glass is provided that effects a transparency as high as possible for operating radiation in the ultraviolet spectral range above 210 nm together with low transparency in the wavelength range below about 190 nm. The filter material of doped quartz glass includes at least 99 wt. % of $SiO_2$ and $Al_2O_3$, wherein the $Al_2O_3$ portion is in the range of 2 wt. % to 4 wt. The filter material has an edge wavelength at a wavelength below 190 nm and a spectral transmission of 80% $mm^{-1}$ or higher at a wavelength of 210 nm.

13 Claims, 2 Drawing Sheets

(51) Int. Cl.
*A61L 9/20* (2006.01)
*A61N 5/06* (2006.01)

(52) U.S. Cl.
CPC .............. *A61N 2005/0654* (2013.01); *A61N 2005/0661* (2013.01); *A61N 2005/0667* (2013.01)

(58) Field of Classification Search
USPC .......... 250/504 R, 492.1, 493.1, 503.1, 365, 250/461.1; 356/51
See application file for complete search history.

(56) References Cited

U.S. PATENT DOCUMENTS

2011/0189389 A1* 8/2011 Yamada .................. B05D 5/06
427/162
2012/0056106 A1* 3/2012 Neumann ................. C03C 3/06
250/492.1
2012/0148770 A1 6/2012 Rong et al.
2013/0095261 A1* 4/2013 Ahn ......................... C03C 3/06
428/34.4

FOREIGN PATENT DOCUMENTS

| DE | 102013204815 A1 | 9/2014 |
| EP | 0822167 A2 | 2/1998 |
| WO | 9009032 A1 | 8/1990 |
| WO | 2010112311 A1 | 10/2010 |

OTHER PUBLICATIONS

Godmanis et al., "Exciton-Phonon Interaction in Crystalline and Vitreous SiO2", Phys. Stat. Sol. (b), vol. 116, Issue 1, pp. 279-287 (Mar. 1983).

* cited by examiner

UV LAMP AND METHOD FOR IRRADIATING A SURFACE, A LIQUID OR A GAS WITH UV RADIATION

BACKGROUND OF THE INVENTION

The present invention relates to a UV lamp for operating radiation with wavelengths in the ultraviolet spectral range and with an optical path in which a filter material of doped quartz glass is provided.

Moreover, the present invention relates to a method for irradiating a surface, a liquid or a gas with UV radiation.

UV lamps in the form of discharge lamps, such as deuterium, halogen, excimer or mercury-vapor lamps, are for instance used for medical and therapeutic applications, in material processing, for sterilization and in spectroscopic devices. These UV lamps have a UV radiation source for emitting UV radiation. UV radiation encompasses the wavelength range of 100 nm to 380 nm according to DIN 5031, Part 7. Before the radiation emitted by the UV radiation source impinges on the item to be irradiated, it passes through a beam exit window. This is a lamp bulb which surrounds the UV radiation source (or a part thereof), or for instance, a cladding tube which surrounds the lamp bulb (or a part of a cladding tube of this nature).

Besides the desired UV operating radiation, the emission spectrum of UV lamps often includes a portion of shortwave ultraviolet radiation having wavelengths below 190 nm that lead to the formation of ozone and can be detrimental to health or induce material to age. Moreover, ozone itself has an absorption band with a maximum wavelength of around 255 nm, which can reduce the intensity of the UV operating radiation.

Quartz glass is transparent to UV radiation over a wide wavelength range and is therefore, in principle, suited as a material for the beam exit window. The transmission of quartz glass depends on the temperature. In the shortwave wavelength range between 140 nm and 200 nm, it is substantially defined by an absorption edge, the so-called Urbach edge (I. T. Godmanis, A. N. Trukhin, K. Hübner "Exciton-Phonon Interaction in Crystalline and Vitreous $SiO_2$", Phys. Stat. Sol. (b), 116 (1983), 279-287). The Urbach edge shifts with a rising temperature toward longer wavelengths. However, at the typical lamp operating temperatures (above 100° C.), it is still within much shorter wavelengths than 190 nm. It is thus not suited for preventing the formation of ozone.

That is why deuterium lamps often use a lamp bulb consisting of a special borosilicate glass, a so-called "UV glass", which absorbs radiation with a wavelength below 190 nm. Borosilicate glass, however, does not show a particularly steep absorption profile, but rather the profile flattens towards the longer-wave range, which reduces transmission in the region of the operating wavelength such that a spectral transmission of less than 80% $mm^{-1}$ is normally obtained at a wavelength around 210 nm.

Deuterium lamps emit UV radiation in the wavelength range of about 180 nm to 380 nm in the form of a continuous, substantially line-free spectrum, and are therefore preferred radiation sources for UV spectroscopy. A high optical stability in the sense of a time-constant emission is demanded from high-quality spectral analyzers. Here, lamp bulbs of borosilicate glass show another weakness. That is, their optical transmission for the UV operating radiation is considerably decreasing in the course of time.

Quartz glass is less prone in this respect. Moreover, quartz glass can be processed more easily than borosilicate glass and exhibits an improved temperature resistance. To reduce the formation of ozone, it is common in deuterium lamps with a lamp bulb of quartz glass to cover the exit window with a multilayered coating which acts as an interference filter for wavelengths below 190 nm. With the help of such interference layers, it is possible to produce a steep absorption edge between a stopband and a passband at a defined edge wavelength. Such a UV lamp is known, for instance, from DE 39 02 144 A1, where the beam exit window is configured over a part of the lamp bulb circumference.

Interference filters of this nature consist of a multitude of thin material layers. The application of the material layers onto the lamp bulb is time-consuming and material-intensive.

It is also known that undesired portions of the UV radiation in the emission spectrum of a lamp are filtered out by doping the glass of the beam exit window with substances that absorb in the wavelength range in question. Titanium dioxide, for instance, is used as a dopant in quartz glass and produces an absorption band with an absorption maximum at about 200 nm. Instead of or in addition to this, International Application Publication No. WO 2010/112311 A1 suggests a filter material consisting of a quartz glass doped with gallium oxide.

In quartz glasses doped with titanium oxide or gallium oxide, the edge wavelength $\lambda_c$ is in the wavelength range of 230 to 250 nm. They are not suited as a filter material for an operating radiation in the wavelength range around 210 to 230 nm.

DE 10 2013 204 815 A1 describes rare earth-doped fiber lasers. The increase in refractive index caused by rare-earth doping is compensated by co-doping with fluorine. Doping with rare-earth metal oxide and $Al_2O_3$ is carried out at different mole fractions. Rare earth metal-doped glasses of this nature show strong absorptions in the UV and VUV range and are suited as filter glasses for filtering out the UV wavelength range.

EP 0 822 167 A2 is concerned with a preform for optical quartz-glass fibers with an $Al_2O_3$-doped fiber core. The homogeneously doped fiber core may contain up to 1.3 wt. % $Al_2O_3$. Higher amounts will lead to crystallization during fiber drawing. Fiber cores with a central dip in the $Al_2O_3$ concentration can also have higher $Al_2O_3$ contents of up to 2.35 wt. % outside their "centerline".

DE 647 537 C describes transition glasses for producing a melting of tungsten or molybdenum current feeds in lamp bulbs. The glasses contain 65-96% $SiO_2$ and between 4-20% $Al_2O_3$ and optionally further oxides. Indicated is a set often transition glasses, whose coefficient of expansion will increase step by step.

U.S. Patent Application Publication No. 2012/0148770 A1 describes packaging glass for pharmaceutical products. The glass contains between 82 and 99.9999 wt. % $SiO_2$, and the residue is formed by dopants, such as $Al_2O_3$. The $Al_2O_3$-doped quartz glass is distinguished by high chemical resistance and moderate viscosity.

In view of the above-explained weaknesses of former filter materials for beam exit windows of UV lamps, the use of doped quartz glass would per se be an appropriate measure for achieving a filter action in an inexpensive and reproducible manner.

However, suitable dopants are not readily available for producing the desired absorption without having a simultaneous impact on the transparency for the operating radiation. Moreover, doping may cause unwanted changes in the quartz glass properties. Specifically, doping can change the viscosity and thermal stability of the quartz glass, increase its tendency to crystallization and reduce the radiation resistance to UV radiation. The latter has a particularly disadvantageous effect especially in quartz glass for UV lamps, because UV radiation damage causes a gradual decrease in UV transmission (aging) and thus a decreasing UV emission.

It is therefore an objective of the present invention to provide a UV lamp having a beam exit window containing filter material of doped quartz glass, wherein doping, on the one hand, does not significantly impair the resistance of the quartz glass to crystallization and temperature, but, on the other hand, effects maximum transparency for operating radiation in the ultraviolet spectral range above 210 nm together with little transparency in the wavelength range below about 190 nm.

Moreover, it is an objective of the present invention to provide a method for effective irradiation of a surface, a liquid or a gas by means of UV radiation together with minimal ozone formation.

BRIEF SUMMARY OF THE INVENTION

One embodiment of the present invention is directed to a UV lamp having an optical path in which a filter material of doped quartz glass is provided. The doped quartz glass includes at least 99 wt. % of $SiO_2$ and $Al_2O_3$, wherein the $Al_2O_3$ portion is in the range of 2 to 4 wt. %. The edge wavelength of the doped quartz glass is at a wavelength below 190 nm and the spectral transmission of the doped quartz glass is 80% $mm^{-1}$ or higher at a wavelength of 210 nm.

BRIEF DESCRIPTION OF THE SEVERAL VIEWS OF THE DRAWINGS

The foregoing summary, as well as the following detailed description of the invention, will be better understood when read in conjunction with the appended drawings.

DETAILED DESCRIPTION OF THE INVENTION

Figure 1:
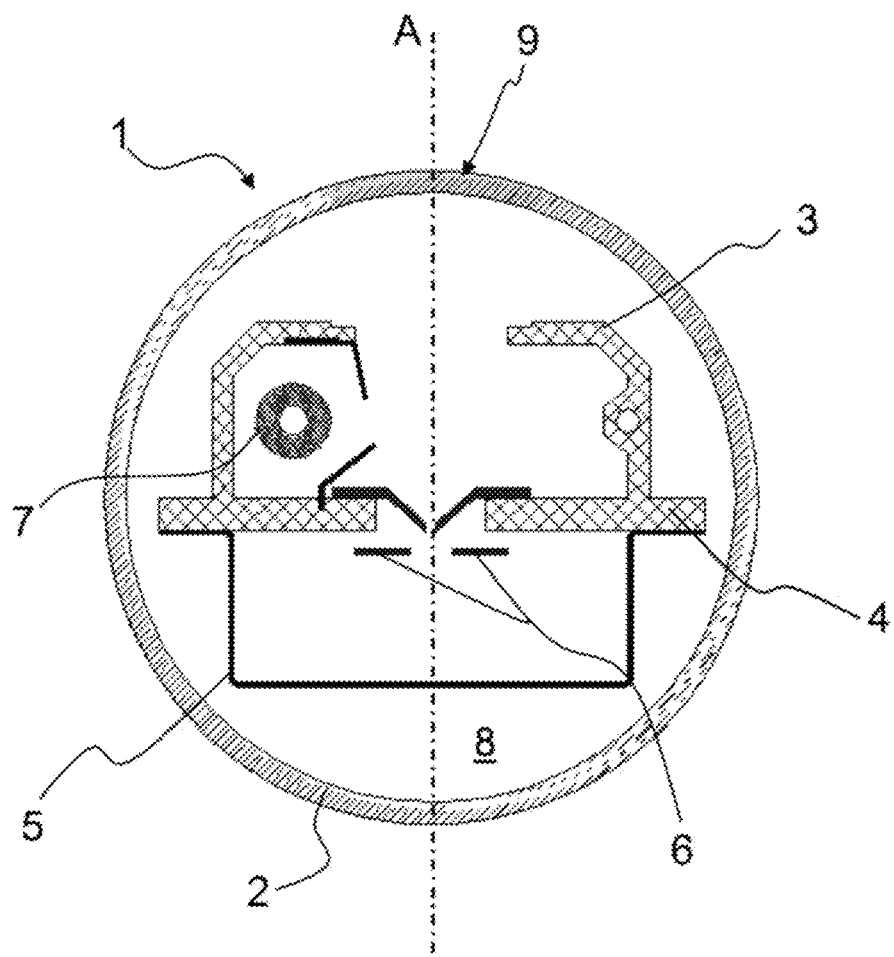
FIG. 1 is a schematic cross-sectional representation of a deuterium lamp in accordance with one embodiment of a UV lamp according to the present invention.

One embodiment of the present invention is directed to a UV lamp having an optical path in which a filter material of doped quartz glass is provided. The doped quartz glass comprises at least 99 wt. % of $SiO_2$ and $Al_2O_3$, wherein the $Al_2O_3$ portion is in the range of 2 to 4 wt. %. The edge wavelength of the doped quartz glass is at a wavelength below 190 nm and the spectral transmission of the doped quartz glass is 80% $mm^{-1}$ or higher at a wavelength of 210 nm.

The optical path of the UV lamp is defined by the geometric profile of the operating radiation starting from the light source proper up to the beam exit out of the lamp. The operating radiation is guided along the optical path onto the object to be treated, processed or measured and passes through the optical filter material of doped quartz glass positioned in the optical path. The filter material is present in the optical path of the UV lamp as a layer or a separate component, such as a filter, or it forms a lamp bulb or a cladding tube of the UV lamp or a part thereof.

Quartz glass is here understood as a highly siliceous glass with a $SiO_2$ portion of at least 95 wt. %. Depending on the concentration of the dopant, the spectral transmission profile of the quartz glass doped with $Al_2O_3$ (aluminum oxide) shows an S-shaped absorption edge with a 50% value (based on the maximum transmission) in the range of 170 nm to about 200 nm. This absorption edge is also called "Urbach edge".

By comparison with undoped quartz glass, it has surprisingly been found that the doping of the quartz glass with $Al_2O_3$ causes a shift of the Urbach edge toward longer wavelengths without having a significant impact on the edge steepness and the transmission of the doped quartz glass in the UV wavelength range of about 200 nm to 250 nm. This effect, however, only becomes noticeable at relatively high $Al_2O_3$ concentrations of about 1 wt. % and more. This explains why the effect has so far not been described in the literature although aluminum oxide is a standard dopant of quartz glass, because at a low concentration in the ppm range, it has a stiffening effect on the network structure of quartz glass, thereby increasing viscosity and thermal resistance. $Al_2O_3$, however, is either used as a co-dopant, so that the shift of the Urbach edge toward longer wavelengths is not noticeable because it is superposed by the other dopants, or these increase the transmission of the doped quartz glass in the UV wavelength range of about 200 nm to 250 nm. Alternatively, this optical filtering effect of the $Al_2O_3$ doping is not relevant to the specific application and has therefore also not been noticed.

At high concentrations of from 2 wt. % up to and including 4 wt. %, aluminum oxide in quartz glass surprisingly shows an absorption in the UV wavelength range that becomes noticeable as a steep absorption edge. Depending on the aluminum concentration of the quartz glass, the so-called edge wavelength λc is in the wavelength range of about 170 to 200 nm, with the absorption edge assuming a longer wave with an increasing aluminum oxide concentration.

The absorption increase for wavelengths of around 200 nm and more remains small, so that a high light transmission is maintained for the standard UV operating radiation up to about 380 nm. The spectral transmission at the wavelength of 210 nm can serve as a measure thereof, the transmission being 80% $mm^{-1}$ or higher for the filter material of the UV lamp according to the present invention. This minimum value for the transmission just serves as a measure of high transparency in the UV wavelength range of 200 to 380 nm.

The optical filtering effect of the $Al_2O_3$ doping in relation to the reduction of the emission of the short-wave UV portion of the UV radiation source and the reduction of the ozone formation depends on the concentration of the aluminum oxide and the transmitted layer thickness. At a small layer thickness, e.g., in the case of a layer applied by vaporization or sputtering with thicknesses in the μm range, comparatively high concentrations of aluminum oxide are required for effecting a significant absorption, and low concentrations at a great layer thickness. For standard window and lamp bulb thicknesses in the range of about 0.5 mm to a few millimeters, the quartz glass of the filter material contains aluminum oxide in a concentration in the range of 2 wt. % up to and including 4 wt. %.

For instance, an aluminum oxide concentration of about 2.7 wt. % and a transmitted material layer thickness of 1 mm yield a spectral position of the absorption edge at a wavelength of about 180 nm (see FIG. 2), but with the advantage of a flank of the absorption edge that is steeper by comparison with borosilicate glass. With an increasing aluminum oxide concentration, the absorption edge shifts further to 200 nm. If an almost complete absorption of short-wave UV radiation is to be achieved in the wavelength range below 190 nm, concentrations at the upper range limit of about 4 wt. % are preferred. The reason is that at higher aluminum oxide concentrations, an increasing absorption is also attained in the longer-wave range.

The filter material of aluminum oxide-doped quartz glass is thus distinguished by a spectral transmission profile that, on the one hand, allows an effective irradiation in the UV wavelength range and, on the other hand, substantially absorbs UV radiation with wavelengths of <190 nm. This is achieved through the position of the edge wavelength $\lambda_c$ and the steepness of the absorption flank that is obtained due to doping of the quartz glass with aluminum oxide. The optical filter material is therefore qualified to reduce the short-wave portion of the UV emission of a UV radiation source, and thereby to prevent the formation of ozone. It is particularly suited for the production of lamp material for UV lamps, e.g., as a lamp tube or as a cladding tube. A high emission and transparency in the wavelength range of about 210 to 380 nm is particularly relevant for deuterium lamps that represent a particularly preferred field of application for the filter material of the present invention.

An optimal effect regarding ozone prevention and transparency for the UV operating radiation is achieved when the filter material has an edge wavelength at a wavelength in the range of 180 to 190 nm.

At least the $SiO_2$ portion of the aluminum oxide-doped quartz glass is produced preferably synthetically.

The oxidative or hydrolytic synthesis of $SiO_2$ from vaporous or liquid start substances by way of gas phase deposition or sol-gel technique is generally known. Synthetically produced quartz glass is distinguished by high transmission in the range of the typical UV operating wavelengths and by high UV radiation resistance. However, the aluminum oxide portion of the quartz glass may possibly lead to the formation of oxygen deficiency defects. Some of these oxygen defects, the so-called "ODC I-defects" ("oxygen deficiency defects") show an absorption band at a wavelength of 164 nm. In combination with the aluminum-oxide doping of the quartz glass, this absorption can influence the spectral position of the absorption edge. It is also known that ODC I-defects exposed to UV radiation can change into other structural defects, particularly into so-called "E' centers", a silicon atom with an unpaired electron. "E' centers", however, show a strong absorption at a wavelength of about 215 nm, which reduces the transparency of the aluminum oxide-doped quartz glass for the UV operating radiation. Surprisingly, however, this undesired conversion in the case of the aluminum oxide-doped filter material does not occur, or occurs to a comparatively small extent, especially when it is used in a deuterium lamp. A possible explanation for this shall be discussed in more detail further below.

Synthetically produced quartz glass often has a high hydroxyl group content that may lead to a reduction of the thermal resistance of the aluminum oxide-doped quartz glass. To avoid this drawback, the quartz glass for the filter material advantageously has a hydroxyl group content of less than 200 wt. ppm, preferably less than 10 wt. ppm.

In a particularly preferred embodiment, the UV lamp comprises a beam exit window which consists of the aluminum oxide-doped quartz glass or which is coated with the aluminum oxide-doped quartz glass.

The service life of the UV lamp is here influenced by the material of the beam exit window, but also by an effect known as "gas consumption". This effect particularly occurs in deuterium lamps and is based on the fact that components diffuse from the lamp filling gas or the electrodes into the lamp bulb, namely preferably into the very hot beam exit window, so that the chemical composition of the beam exit window will gradually change.

To counteract this effect, it has been found to be advantageous that the beam exit window is coated with a layer of aluminum oxide at its side facing a lamp interior.

The layer of aluminum oxide acts as a barrier against the in-diffusion of components from the filling gas or the electrodes into the material of the beam exit window. The layer of aluminum oxide reduces, for instance, the reaction of a possible coating compound on the cathode with the quartz glass of the beam exit window. Preferably, the diffusion barrier layer contains amorphous aluminum oxide, has a thickness in the range of 20 to 200 nm and is optically transparent to UV radiation.

The UV lamp according to an embodiment of the invention emits operating radiation which encompasses the wavelength of 210 nm. It is, for instance, used for irradiating a surface, a liquid or a gas, in which processed foodstuff, air, liquids or the surfaces of technical items are effectively sterilized, varnish or plastic layers are cured, and medical, dental or therapeutic irradiations or spectroscopic measurements on gases or liquids are carried out. The deuterium lamp is a preferred embodiment of the UV lamp.

The "Urbach edge" can be shifted with a rising temperature of the beam exit window toward longer wavelengths. A temperature increase of 100° C. causes approximately a shift by 2 nm to 3 nm. Since the beam exit window is kept at an operating temperature in the range of 250° C. to 350° C., the Urbach edge can be shifted independently of the displacement effect by the aluminum oxide doping by approximately another 6 to 9 nm into the long-wave range and the ozone formation can be further reduced. If the nominal operating temperature during UV irradiation is known, this effect can be taken into account in the measurement of the dopant concentration when an exact position of the Urbach edge is of relevance.

The present invention also relates to an irradiation method in which the optical filter material of doped quartz glass is used. Specifically, the optical fiber material of doped quartz glass includes at least 99 wt. % of $SiO_2$ and $Al_2O_3$, wherein the $Al_2O_3$ portion is in the range of 2 to 4 wt. %. The filter material has an edge wavelength of below 190 nm and a spectral transmission of 80% $mm^{-1}$ or higher at the wavelength of 210 nm.

A UV lamp according to an embodiment of the present invention is suited for performing the irradiation method according to the present invention. The UV operating radiation is guided through a filter material of quartz glass with $Al_2O_3$ doping. By comparison with undoped quartz glass, this aluminum oxide doping causes a shift of the Urbach edge to longer wavelengths without having a significant impact on the edge steepness and the transmission in the UV wavelength range of about 200 nm to 250 nm. The reason is that at concentrations of from 2 wt. % up to and including 4 wt. %, aluminum oxide in quartz glass surprisingly shows an absorption in the UV wavelength range that becomes noticeable as a steep absorption edge with an edge wavelength λc in the wavelength range of about 170 to 200 nm. This shift of the absorption edge leads to a reduction of ozone formation in the UV irradiation method with a UV operating radiation in the range of 200 to about 380 nm. The absorption increase remains small for wavelengths of about 200 nm and more, so that a high light transmission is maintained for the UV operating radiation. As a measure of this, the spectral transmission can be used at the wavelength of 210 nm, which is 80% mm$^{-1}$ or higher for the transmission.

The optical filter material is therefore suited for reducing the short-wave portion of the UV emission of a UV radiation source and thereby prevents the formation of ozone. The UV irradiation method according to an embodiment of the present invention using this filter material therefore allows, on the one hand, an effective irradiation in the UV wavelength range, whereby, on the other hand, UV radiation with wavelengths <190 nm and thus the formation of ozone is substantially prevented.

FIG. 1 schematically shows a deuterium lamp 1 in cross section along the optical axis A. The lamp 1 comprises a lamp bulb 2 which encloses an interior 8 filled with deuterium. The interior 8 contains a two-part housing which includes a front housing part 3 with a cathode 7 arranged therein, a housing partition 4 of aluminum oxide, and a rear housing part 5 of metal in which an anode 6 is disposed. A light exit opening 9, which is highlighted by gray shading in FIG. 1, is provided on the front housing part 3. This area of the lamp bulb 2 represents a "beam exit window" within the meaning of the present invention. Upon ignition of a discharge between cathode 7 and anode 6, a light cone will pass along the optical axis A onto the light exit opening 9.

The whole lamp bulb 2, including its circumferential portion serving as a beam exit window 9, consists of synthetically produced quartz glass that is homogeneously doped with aluminum oxide in a concentration of 2.7 wt. %.

The inside of the lamp bulb 2 facing the interior 8 is completely coated with a diffusion barrier layer (not plotted) of amorphous Al$_2$O$_3$. The diffusion barrier layer is applied by dip coating in the sol-gel dipping process, dried and burnt in at 900° C. for 12 h. It is thereafter transparent in the wavelength range between 100 and 1100 nm and has a thickness of 100 nm. The diffusion barrier layer reduces the out-diffusion of components of the filling gas and the electrode coating and their reaction with the material of the lamp bulb 2, namely particularly in the area of the light exit opening 9 which is particularly hot during lamp operation.

Figure 2:
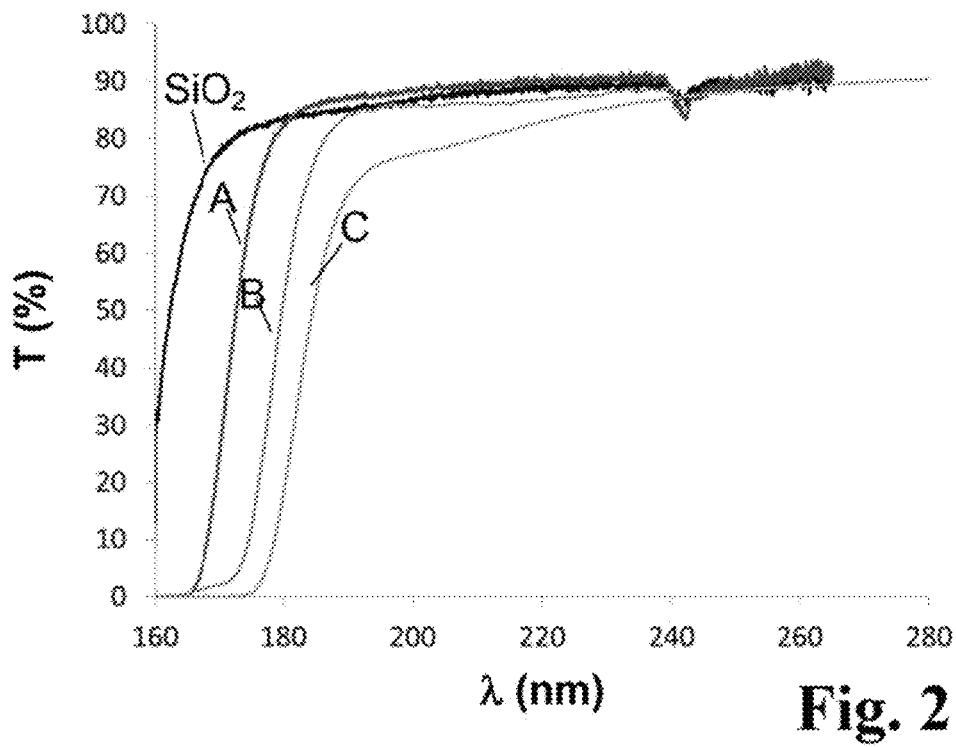
FIG. 2 is a diagram of transmission curves of various aluminum oxide-doped quartz glasses according to an embodiment of the invention as compared with transmission curves of an undoped quartz glass and a commercial UV glass (borosilicate glass)

The aluminum oxide doping of the lamp bulb 2 causes a shift of the Urbach edge of the quartz glass, as impressively demonstrated by the transmission spectra of FIG. 2. On the the measured transmission T (in %) is plotted against the wavelength λ (in nm) over the wavelength range of 160 to about 280 nm. The "measured transmission" T includes reflection losses on surfaces and differs in this respect from the so-called "internal transmittance".

The diagram of FIG. 2 shows transmission profiles of two filter material samples of SiO$_2$—Al$_2$O glass which differ in their aluminum oxide content from each other, as follows: Sample A: 98.9 SiO$_2$/1.1 Al$_2$O$_3$; Sample B: 97.3 SiO$_2$/2.7 Al$_2$O$_3$. Moreover, for comparison, the transmission profile of a commercial, synthetically produced and undoped quartz glass (curve SiO$_2$: trade name "Suprasil 1") and the transmission profile of a commercial borosilicate glass (curve trade name: Schott 8337B) are plotted.

The edge wavelength $\lambda_c$ at room temperature and the transmission value T (210 nm) determined at the wavelength 210 nm, as well as the respective sample thickness, are summarized in the following Table 1 for the measurement samples.

TABLE 1

| Sample/curve | λc [nm] | T(210 nm) [%] | Sample thickness [mm] |
|---|---|---|---|
| SiO$_2$ | 163 | 88 | 1 |
| A | 172 | 89 | 1 |
| B | 179 | 86 | 1 |
| C | 183 | 79 | 0.3 |

It can be seen from the transmission curves A and B that doping with aluminum oxide causes a shift of the edge wavelength $\lambda_c$ by comparison with pure SiO$_2$. A doping concentration of 1.1 wt. % (Sample A) yields a shift of the absorption edge by about 9 nm. With an increasing dopant concentration, the absorption edge shifts further towards longer wavelengths without a substantial change in the steepness of the absorption edge and the transmission value T (210 nm), which is here selected as a representative.

At an Al$_2$O$_3$ concentration of 2.7 wt. % (curve B), the absorption edge of the doped quartz glass shows, at a transmitted material layer thickness of 1 mm, a spectral position at a wavelength around 179 nm, i.e. it has a slightly shorter wave than the one of the borosilicate UV glass (curve C) at a transmitted material layer thickness of 0.3 mm. In the case of curve B, however, the absorption edge is slightly steeper than in the case of curve C, and specifically the representative transmission value T (210 nm) is at 86% higher than in the case of the UV glass (about 79%). In this connection, it should be noted that the measurement thickness of Sample C is only 0.3 mm. The small measurement thickness is needed for achieving a transmission value comparable to the other samples in the representative wavelength range (e.g. T (210 nm)), which reduces the formation of ozone.

At an aluminum oxide concentration of 4 wt. % (not included in the diagram), a further shift of the Urbach edge manifests itself, with the transmission for the wavelength range <180 nm being reduced to values below 5%. Although due to the comparatively high dopant concentration, the absorption edge is slightly flatter than in the UV glass of Sample C, it reaches a higher maximum transmission with a T (210 nm) value around 80%.

To test the long-term stability of the aluminum oxide-doped quartz glass under typical operation conditions of a deuterium discharge lamp, windows in the size of the beam exit window 9 were respectively manufactured from the materials of Samples A and B of Table 1 and tightly molded in the area of the beam exit window 9 into the lamp bulbs 2 of undoped quartz glass. The inside of the lamp bulb 2 was then provided with a layer of amorphous Al$_2$O$_3$, as has been explained above, and the lamp bulb was again filled with the nominal filling gas. The deuterium lamp modified in this way was operated for 2000 hours in a temperature conditioning unit customary for liquid chromatography, and the radiation density was measured from time to time on a calibrated testing facility in a spectrally resolved manner.

Figure 3:
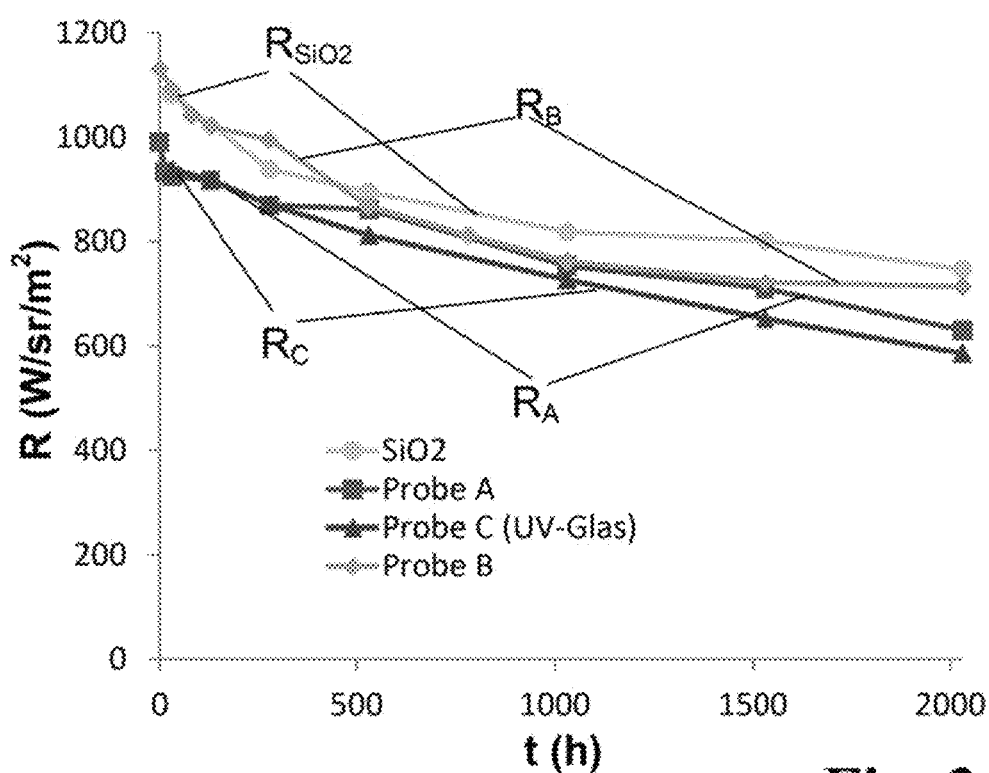
FIG. 3 is a diagram of the time curve of the measured radiation density in the spectral range of 205 to 215 nm for an aluminum oxide-doped quartz glass according to an embodiment of the invention as compared with that of a commercial UV glass (borosilicate glass).

The diagram of FIG. 3 shows the result of this measurement as compared to a deuterium lamp with a lamp bulb made from the commercial borosilicate glass (Schott 8337B; curve R$_C$) and a lamp bulb made from the undoped, synthetically produced SiO$_2$ glass (Suprasil 1; curve: R$_{SiO2}$) with a coating of amorphous aluminum oxide. On the y-axis, the specific radiation density R (as absolute value) in the spectral range between 205 and 215 nm (in W/sr/m$^2$) (watt per m$^2$ und per steradian) is plotted as a function of the lamp operation duration t (in h).

It is apparent from FIG. 3 that the measured radiation density R is decreasing in all lamps first approximately congruently. The lamp with the lamp bulb of pure SiO$_2$ exhibits the smallest loss of radiation density (but is accompanied by the formation of ozone). In the commercial deuterium lamp of UV glass (curve R$_C$) and in the UV lamp with the lamp bulb of 98.9% SiO$_2$/1.1% Al$_2$O$_3$ (curve R$_A$), the measured radiation density is continuously decreasing, especially also during the interval between 1000 and 1500 operating hours, whereas in the deuterium lamp equipped with the aluminum oxide-doped quartz glass window 97.3% SiO$_2$/2.7% Al$_2$O$_3$ (curve R$_B$), the measured radiation density between 1000 and 1500 operating hours seems to settle at an approximately constant level.

Especially the quartz glass of Sample B is particularly suited for use as a filter material or lamp bulb for a light source in a spectrophotometer. Its (measured) spectral transmission at the wavelength of 210 nm is about 86% and at 190 nm it is about 84%. The edge wavelength $\lambda_c$ is about 179 nm at room temperature and is shifted by temperature control of the lamp bulb to a temperature of 300° C. to about 185 to 188 nm, resulting in a small ozone formation.

The manufacture of the filter material from aluminum oxide-doped quartz glass shall be explained with reference to an example.

A slurry of discrete SiO$_2$ particles with a mean particle size of about 10 μm is prepared in ultrapure water. An amount of 285.7 g of the slurry with a residual moisture of 37.4% is diluted with 1000 ml ultrapure water. A pH of 14 is set by adding a concentrated ammonia solution in an amount of 75 ml. The alkaline suspension is homogenized and filtered off through a 25 μm membrane filter.

An aqueous suspension of 62.71 g AlCl$_3$ is prepared in 400 ml of ultrapure water and also filtered off through a 15 μm membrane filter. Instead of AlCl$_3$, other aluminum-containing start substances may also be used, such as for example, organic Al compounds, nitrides or fluorides.

The suspension which is moved by stirring is fed with the dopant solution in the fibrin of an atomized spray for a period of 65 minutes. To produce the atomized spray, the dopant solution is atomized by means of a spray nozzle, with an operating pressure of 2 bar and a flow rate of 0.8 l/h being set. The atomized spray produced in this way contains droplets with a mean diameter between 10 μm and 40 μm. Subsequently, the doped slurry is homogenized by stirring for another 2 hours. With this procedure, it is ensured that an optimally homogeneously doped SiO$_2$ slurry is obtained.

The doped SiO$_2$ slurry is frozen and further processed by way of so-called freeze granulation into a granulate. The slurry made of the granulate, which is obtained after unfreezing, is repeatedly washed with ultrapure water and the excess water is decanted each time.

Subsequently, the granulate slurry which is freed from ammonia and purified is dried at a temperature of about 400° C. for 6 hours. The dried granulate is sealed in a plastic mold and isostatically pressed at 400 bar.

The pressed body made of the granulate which is thereby obtained is heated under helium flushing and is subsequently treated in a chlorine-containing atmosphere at about 900° C. for about 8 hours. Impurities are thereby removed from the pressed body and the hydroxyl group content is reduced to less than 200 wt. ppm, preferably to less than 10 wt. ppm.

The purified pressed body made of the granulate is subsequently pre-sintered by heating it in a vacuum furnace (<1 mbar) up to a temperature of 1550° C. Sintering into a body of transparent glass is carried out in an argon atmosphere by gas pressure sintering. During a first phase of nine hours, which comprises heating up and the first three hours of the hold time at that temperature, a vacuum (<5 mbar) is maintained in the sintering furnace, interrupted by inert-gas flushing operations. During a second phase, an argon overpressure of 15 bar is produced and the furnace temperature is raised to 1680° C. At this temperature, the pre-sintered body is vitrified into a block of transparent quartz glass for a period of 1 h and is subsequently cooled.

The following are definitions for various terms or phrases recited herein.

Optical path: The optical path of the UV lamp is defined by the geometric profile of the operating radiation, starting from the light source proper up to the beam exit out of the lamp. The optical path comprises a beam exit window through which the radiation emitted by the UV lamp passes before impinging on the item to be irradiated.

Quartz glass: Quartz glass means here a highly siliceous glass with a SiO$_2$ portion of at least 93 wt. %.

Edge wavelength: The edge wavelength $\lambda_c$—here also called absorption edge—corresponds to the wavelength at which the spectral internal transmittance coefficient is half the maximum difference of the spectral internal transmittance coefficients of stopband and passband.

Transmission: The spectral internal transmittance coefficient (also called "internal transmittance") does not include reflection losses and is by definition understood as the ratio of the outgoing spectral radiation flux to the radiation flux that has entered. By contrast, the "measured transmission" includes reflection losses on surfaces.

Spectral radiation density: The spectral radiation density of a body is defined in DIN EN ISO 9288. It indicates which radiant power the body emits at a frequency into the direction given by a polar angle and the azimuth angle per projected area, per spatial angle and per frequency width.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A UV lamp for operating radiation with wavelengths in the ultraviolet spectral range, the UV lamp comprising:
    an optical path in which a filter material of doped quartz glass is provided,
    wherein the doped quartz glass includes at least 99 wt. % of SiO$_2$ and Al$_2$O$_3$, the Al$_2$O$_3$ portion being in the range of 2 wt. % to 4 wt. %,
    wherein the filter material has an edge wavelength at a wavelength below 190 nm, and
    wherein the filter material has a spectral transmission of 80% mm$^{-1}$ or higher at a wavelength of 210 nm.

2. The UV lamp according to claim 1, wherein the doped quartz glass has a hydroxyl group content of less than 200 wt. ppm.

3. The UV lamp according to claim 1, wherein a beam exit window is provided that consists of the filter material of the doped quartz glass or is coated with the doped quartz glass.

4. The UV lamp according to claim 3, wherein the beam exit window is coated with a layer of amorphous aluminum oxide at its side facing a lamp interior.

5. The UV lamp according to claim 1, wherein the UV lamp is a deuterium lamp.

6. The UV lamp according to claim 1, wherein the filter material has an edge wavelength at a wavelength in the range of 180 to 190 nm.

7. The UV lamp according to claim 1, wherein the doped quartz glass of the filter material contains synthetically produced $SiO_2$.

8. The UV lamp according to claim 1, wherein the doped quartz glass of the filter material has a hydroxyl group content of than 1 wt. ppm.

9. A method for irradiating a surface, a liquid or a gas with UV radiation using an optical filter material of doped quartz glass, the method comprising:

guiding the UV radiation through the optical filter material of doped quartz glass, wherein the doped quartz glass includes at least 99 wt. % of $SiO_2$ and $Al_2O_3$, the $Al_2O_3$ portion being in the range of 2 wt. % to 4 wt. %, wherein the optical filter material has an edge wavelength at a wavelength below 190 nm, and wherein the optical filter material has a spectral transmission of 80% $mm^{-1}$ or higher at a wavelength of 210 nm.

10. The method according to claim 9, wherein at least the $SiO_2$ portion of the doped quartz glass is synthetically produced.

11. The method according to claim 9, wherein the doped quartz glass has a hydroxyl group content of less than 200 wt. ppm.

12. The method according to claim 11, wherein the doped quartz glass has a hydroxyl group content of less than 1 wt. ppm.

13. The UV lamp according to claim 2, wherein the doped quartz glass has a hydroxyl group content of less than 10 wt. ppm.

* * * * *